(12) United States Patent
Hamazaki et al.

(10) Patent No.: US 7,300,083 B2
(45) Date of Patent: Nov. 27, 2007

(54) TONGS

(75) Inventors: Hidenobu Hamazaki, Naruto (JP); Masahito Hamazaki, Naruto (JP)

(73) Assignee: Masahito Hamazaki, Tokushima (JP)

( * ) Notice: Subject to any disclaimer, the term of this patent is extended or adjusted under 35 U.S.C. 154(b) by 0 days.

(21) Appl. No.: 11/476,670

(22) Filed: Jun. 29, 2006

(65) Prior Publication Data

US 2007/0001471 A1    Jan. 4, 2007

(30) Foreign Application Priority Data

Jul. 1, 2005    (JP)    .............................. 2005/194429

(51) Int. Cl.
B25J 1/02    (2006.01)

(52) U.S. Cl. .......................... 294/118; 294/16; 414/917

(58) Field of Classification Search .................. 294/16, 294/28, 106, 118, 119, 119.1; 414/917; 30/237, 30/239
See application file for complete search history.

(56) References Cited

U.S. PATENT DOCUMENTS

| | | | | |
|---|---|---|---|---|
| 1,611,061 A | * | 12/1926 | Palm | ........................... 30/428 |
| 2,610,890 A | * | 9/1952 | Jaeger | ..................... 294/110.1 |
| 3,069,761 A | * | 12/1962 | Sommer | ...................... 29/252 |
| 3,302,287 A | * | 2/1967 | Kelly | ........................... 30/134 |
| 4,093,298 A | * | 6/1978 | Gatewood | ................... 294/118 |
| 5,795,003 A | * | 8/1998 | Nerger et al. | ............... 294/106 |

FOREIGN PATENT DOCUMENTS

| | | |
|---|---|---|
| JP | 55-129791 | 9/1980 |
| JP | 56-121592 | 9/1981 |
| JP | 58-4384 | 1/1983 |
| JP | 58-10492 | 1/1983 |
| JP | 59-24981 | 2/1984 |
| JP | 60-143687 | 9/1985 |
| JP | 1-295781 | 11/1989 |
| JP | 5-69371 | 3/1993 |
| JP | 8-155852 | 6/1996 |
| JP | 10-118945 | 5/1998 |
| JP | 11-58256 | 3/1999 |
| JP | 11-137562 | 5/1999 |
| JP | 2002-355160 | 12/2002 |

* cited by examiner

*Primary Examiner*—Dean J Kramer
(74) *Attorney, Agent, or Firm*—Wenderoth, Lind & Ponack, L.L.P.

(57) ABSTRACT

A first tong member includes a first 4-joint linkage, in which both pairs of opposite rods are substantially equal, in length, to each other; a second tong member likewise includes a second 4-joint linkage, in which both pairs of opposite rods are substantially equal; and the first and second linkages have one of the foregoing rods in common. The first linkage has a first arm extended from the rod opposite to the common rod, and the second linkage likewise has a second arm extended from the rod opposite to the common rod, so that when respective actuating tails of the first and second tong members are operated in an arcuate manner, an opening width in the article-seizing area is configured to be capable of being adjusted, while the first and second extended arms in a substantially parallel relationship with each other maintain a substantially constant distance defined in between.

9 Claims, 7 Drawing Sheets

TONGS

BACKGROUND OF THE INVENTION

1. Field of the Invention

The present invention relates to tongs for seizing and lifting an article, and specifically to tongs which are suitably utilized as, for example, kitchen tongs, handicraft or other general-purpose working tongs.

2. Description of the Related Art

Figure 11:
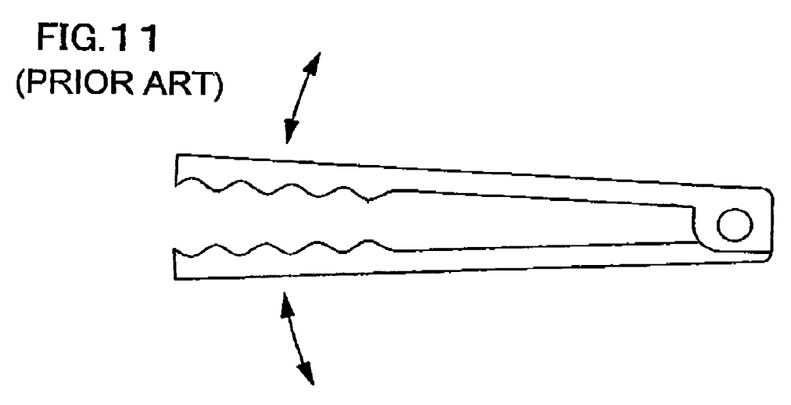
FIG. 11 is a schematic view exemplifying a pair of conventional tweezers.
Figure 12:
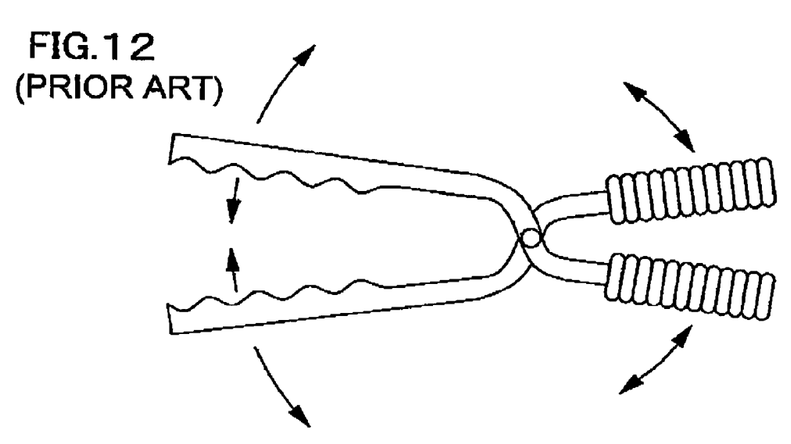
FIG. 12 is a schematic view exemplifying a pair of conventional, scissor-like tongs.

Tongs are an instrument for seizing an article, in which two bars are usually connected pivotably on a single fulcrum. For example, hand-held tongs are commonly used for movement of food products between two locations. Included are sugar tongs, ice tongs and pasta tongs, depending on a type of article to be seized. Publicly known tongs are of a type in which two bars are fastened at one end to be moved into open and closed positions like in a pair of tweezers as shown in FIG. 11, or in which two bars are so pivoted together near a central portion that the bars work one against the other into open and closed positions like in a pair of scissors as shown in FIG. 12. See Unexamined Japanese Patent Application (KOKAI) No. 2002-355160 for example. In the case of the tongs as shown in FIG. 12 for example, the tongs are held by hand like a pair of scissors, in which two handles are operated to open and close the seizing arms of the tongs.

As can be seen from the above, conventional tongs are held by hand to be pivoted on a fulcrum into open and closed positions, so that article-seizing arms are similarly opened and closed in a pivotal manner. As a result, the seizing arms are constantly kept in an angled position tapering into one direction, making it impossible to keep the seizing arms in a parallel relationship with each other.

Figure 13:
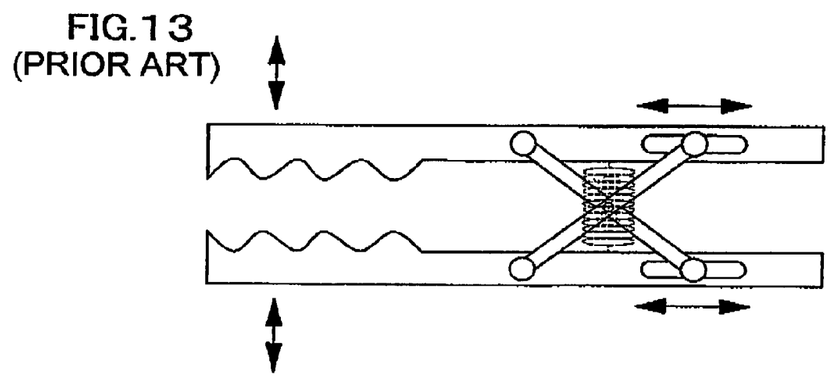
FIG. 13 is a schematic view exemplifying a pair of conventional tongs having a cross-shaped link.

Apart from the above, there has also been developed a mechanism that is capable of seizing an article, keeping its seizing arms substantially in a parallel position. For example, in the case of the tongs as shown in FIG. 13, the left and right handles are interconnected via a cross-shaped link such that an elastic member, such as a spring, is placed in between to facilitate an opening and closing of the two tong members. By manually controlling the direction and strength of the force to be applied while holding the tong members, the illustrated tongs can be moved into opened and closed positions, with the two tong members being kept substantially in a parallel position. However, as compared with a pivotal motion, in the case in which the force is transferred by a sliding motion, a greater width of gap or play may be required in order to reduce a contact frictional resistance generated at the connection point and also to operate the whole mechanism smoothly. Unlike a pivotal type, such a slidable type of tongs have been inherently subject to an operational error or ricketiness. Also, because the tongs in this configuration consist of two bar members in which the seizing arm and the handle portion are integrally formed for each tong member, the tongs have often faced problems that an article larger than the width in the handle portion cannot be held with the seizing arms of the tongs.

The present invention has therefore been made in view of the conventional problems as mentioned above. The major object of this invention is to provide tongs which can be opened and closed in a simplified mechanism allowing the seizing arms to be kept in a parallel position, yet without spoiling an advantage of easy openability and closeability similar to scissors.

SUMMARY OF THE INVENTION

To attain the above-mentioned object, the tongs in accordance with the present invention are fabricated in a scissor-like configuration, the tongs being provided with a first tong member which includes both a first shank elongated in one direction and a first arm for seizing and lifting an article, the first arm being extended from an end of the first shank, and also provided with a second tong member which likewise includes both a second shank elongated in one direction and a second arm for seizing and lifting the article, the second arm being extended from an end of the second shank. The first and second tong members are pivotably interconnected on one or more fulcrums, so that a distance in an article-seizing area defined between the first and second extended arms is capable of being adjusted by operating the respective actuating tails of the first and second tong members, the actuating tails being situated respectively on the sides opposite from the extended arms. The first tong member is provided with a first, parallelogrammatic, 4-joint linkage, in which both pairs of opposite rods are configured to be substantially equal, in length, to each other, while the second tong member is provided with a second, parallelogrammatic, 4-joint linkage, in which both pairs of opposite rods are likewise configured to be substantially equal, in length, to each other. The first and second, 4-joint linkages have one of the foregoing rods in common. The first, 4-joint linkage has the first extended arm mounted to the rod opposite to the common rod, while the second, 4-joint linkage likewise has the second extended arm mounted to the rod opposite to the common rod. It is so arranged that, when the respective actuating tails in the first and second tong members are operated in an arcuate manner, an opening width in the article-seizing area is capable of being adjusted, while the first and second extended arms in a substantially parallel relationship with each other maintain a substantially constant distance defined between the two extended arms. By this configuration, when the actuating tails of the first and second tong members are pivoted in an arcuate manner, the seizing area is capable of adjusting the width of its gap, maintaining a parallel position.

The above and other objects and features of the invention will more fully become apparent from the following detailed description when taken in conjunction with the accompanying drawings.

DETAILED DESCRIPTION OF THE PREFERRED EMBODIMENTS

Various embodiments of the present invention will now be described in conjunction with the accompanying drawings. It should be noted, however, that the embodiments to be described below are merely illustrative of the tongs to embody the spirit of the present invention, and that the scope of the present invention is not limited to the tongs described below. Also, in the present disclosure, those members described in the appended claims are, in no way, specified to the members described in the embodiments. Particularly, unless otherwise specifically set forth herein, the scope of the present invention is not contemplated to be limited to but is rather intended to be merely illustrative of the components described in the embodiments, in terms of dimension, material quality, shape, and relative disposition thereof. It should also be noted that the size, locational relationship and the like of the members illustrated in each drawing may be indicated and described in an exaggerated manner for purposes of clarity. Further, in the following description, like names and like numerals designate identical or the same members, a detailed description of which may be suitably omitted. It should also be added that each component constituting the present invention may be either realized in a manner of integrating a plurality of components into the same member to utilize such a member for a plurality of factors, or conversely, may be realized in a manner of sharing a plurality of members to perform a function of one member.

When the terms "top", "bottom", "first", "second", "front", "back", "outer", "upper", "lower", "height", "width", "length", "end", "side", "horizontal", "vertical", "axial", "radial", and similar terms are used herein, it should be understood that these terms have reference only to the structure shown in the drawings as it would appear to a person viewing the drawings and are utilized only to facilitate describing the invention.

In one embodiment, the first tong member includes a first auxiliary link which is provided with a pivot respectively at opposite ends of the auxiliary link, so that the first auxiliary link may be connected with the first tong member at one of the pivots and with the second tong member at the other of the pivots. When so configured, the parallel state in the seizing area can be maintained in a secured manner.

In addition, the second tong member includes a second auxiliary link which is provided with a pivot respectively at opposite ends of the auxiliary link, so that the second auxiliary link may be connected with the second tong member at one of the pivots and with the first tong member at the other of the pivots. By this configuration, the parallel state in the seizing area can be maintained in an even more secure manner.

In another embodiment, the first tong member can have a portion of the first shank configured to be common with one rod which constitutes the first, 4-joint linkage. When so configured, the shank can be utilized to constitute one rod of the first, 4-joint linkage, aiming at a lower cost of manufacture resulting from a simplified structure.

In even another embodiment, the rods adjacent to the common rod in the second, 4-joint linkage can be configured to be longer than those in the first, 4-joint linkage. By this configuration, when the first and second, 4-joint linkages are overlapped with respect to each other, a rod-to-rod contact can easily be avoided.

In still another embodiment, the second, 4-joint linkage can be configured to be in substantially the same shape and dimension as the first, 4-joint linkage. By this configuration, the first and second, 4-joint linkages can be utilized as a common member.

In a further embodiment, the first and second tong members may be adapted to have an aperture defined respectively at the actuating tails of the tong members, so as to accommodate an operator's thumb or finger. By this configuration, the operator's thumb or finger engagement in the apertures will enable the first and second tong members to be easily opened and closed for adjustment of the opening width in the seizing area.

In an even further embodiment, the first and second extended arms may be respectively provided with a cutting blade. By this configuration, the seizing area can serve as a cutting area, where a seized article can be cut out from opposite sides in a parallel manner.

In a still further embodiment, at least one of the first and second extended arms may be provided with a heating element. By this configuration, materials can be thermally processed, keeping the heating element in a parallel manner.

In another embodiment, the inventive tongs are fabricated in a scissor-like configuration, the tongs being provided with a first tong member which includes both a first shank elongated in one direction and a first arm for seizing and lifting an article, the first arm being extended from an end of the first shank, and also provided with a second tong member which likewise includes both a second shank elongated in one direction and a second arm for seizing and lifting the article, the second arm being extended from an end of the second shank. The first end second tong members are pivotably interconnected on one or more fulcrums, so that a distance in an article-seizing area defined between the first and second extended arms is capable of being adjusted by operating the respective actuating tails of the first and second tong members, the actuating tails being situated respectively on the sides opposite from the extended arms. The first tong member includes a first, 4-joint linkage in which an opposed pair of substantially parallel rods are substantially equal, in length, to each other, while the second tong member likewise includes a second, 4-joint linkage in which an opposed pair of substantially parallel rods are substantially equal, in length, to each other. The first, 4-joint linkage has the first extended arm mounted to a rod which is pivotably extended across the opposed pair of substantially parallel rods, while the second, 4-joint linkage likewise has the second extended arm mounted to a rod which is pivotably extended across the opposed pair of substantially parallel rods. The first tong member further includes a first auxiliary link provided with a pivot respectively at opposite ends of the auxiliary link, the first auxiliary link being connected with the first tong member at one of the pivots and with the second tong member at the other of the pivots. Similarly, the second tong member further includes a second auxiliary link provided with a pivot respectively at opposite ends of the second link, the second auxiliary link being connected with the second tong member at one of the pivots and with the first tong member at the other of the pivots. It may be so arranged that, when the respective actuating tails in the first and second tong members are operated in an arcuate manner, an opening width in the article-seizing area is capable of being adjusted, while the first and second extended arms in a substantially parallel relationship with each other maintain a substantially constant distance defined between the extended arms. When so configured, even without a provision of a common rod in the first and second, 4-joint linkage, the opening width in the seizing area is capable of being adjusted, maintaining the substantially parallel relationship.

As described above, in accordance with the inventive tongs, an article can be seized and lifted in a parallel manner by a simple operation of pivoting the actuating tails in an arcuate manner. This arrangement enables the article to be securely seized from opposite sides with equal stresses, avoiding a damage or deformation of the article.

Figure 1:
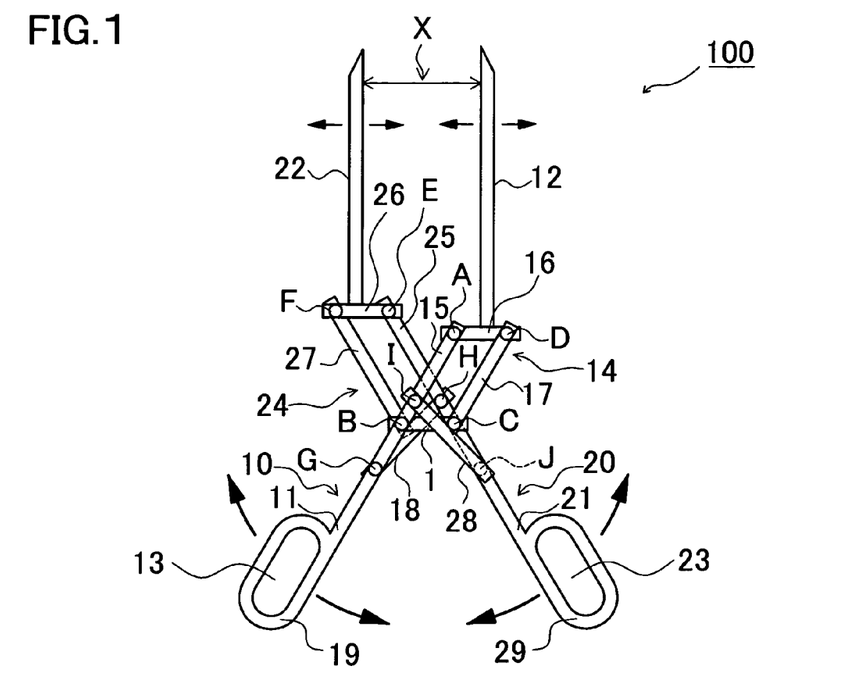
FIG. 1 is a schematic view of the tongs according to a first embodiment of the invention, in which the seizing area is in an open position.
Figure 2:
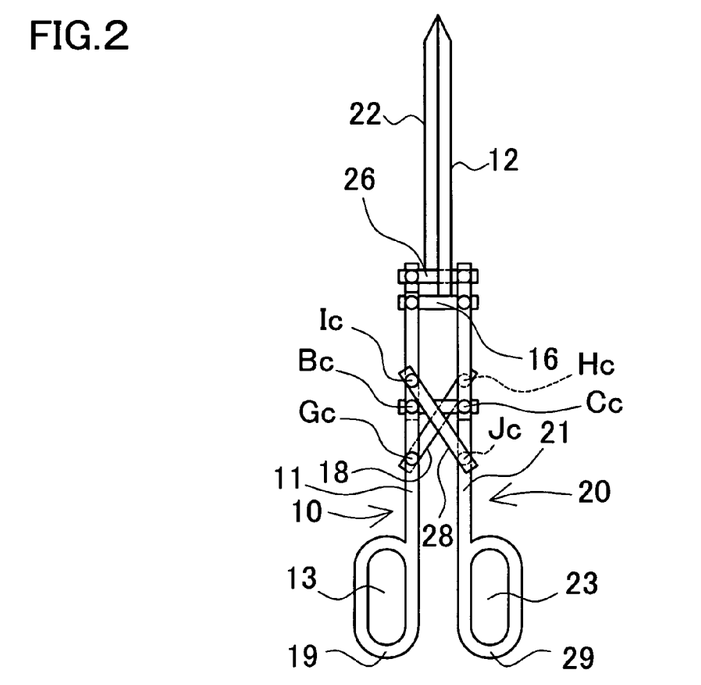
FIG. 2 is a schematic view of the tongs shown in FIG. 1, in which the seizing area is in a closed position.

Illustrated in FIGS. 1 and 2 is a schematic configuration of the tongs 100 according to the first embodiment of the present invention. FIGS. 1 and 2 show the seizing area X in its open and closed positions, respectively. The tongs 100 shown in these figures have the first tong member 10 and the second tong member 20 interconnected pivotably on a plurality of fulcrums. The first tong member 10 is provided with an article-seizing first arm 12 at the front end of the first rod-shaped shank 11, and has an actuating tail 19 formed at the rear end of the first shank 11. Also provided is a first aperture 13 for accommodating an operator's thumb or finger. The second tong member 20 is in substantially the same configuration as the first tong member 10, and is provided with a second arm 22 at the front end of the second shank 21, with a second aperture 23 being formed at the rear end. When the operator's thumb or finger respectively is engaged in the apertures 13, 23 to open and close the actuating tails 19, 29, the seizing area X formed between the first and second tong members 10, 20 can be moved into the open and closed positions by means of a plurality of fulcrums or pivots. In FIG. 1, the first tong member 10 is angled obliquely from the upper right down to the lower left, and the second tong member 20 is angled from the upper left down to the lower right. It will be apparent that the first and second tong members can be arranged to replace with each other.

Further, optionally, an elastic member such as a spring can be interposed between the first and second tong members. The operator can thus manipulate the actuating tails in resistance to the elastic member, so that the seizing area may be biased, between uses, by the elastic members to maintain its closed or open position.

In the connection point serving as a fulcrum for a pivotable or rotatable motion, a bar-shaped pivot stud such as a bolt and a pin may be employed for free rotation about the pivot axis.

The first shank 11 is also provided with a first, parallelogrammatic, 4-joint linkage, in which both pairs of opposite rods are configured to be substantially equal, in length, to each other; likewise, the second shank 21 is provided with a second, parallelogrammatic, 4-joint linkage, in which both pairs of opposite rods are configured to be substantially equal, in length, to each other. The 4-joint linkages 14, 24 have each of its rods connected pivotably about the respective pivot, and the opposing rods can be kept in a parallel relationship even when the angularity formed between the rods is changed. The 4-joint linkages 14, 24 also have one of their rods in common. In the case of FIG. 1, the geometrical bottom base 1 (referred herein to as a lower rod) in the first, 4-joint linkage is common with the lower rod in the second, 4-joint linkage 24. By this configuration, the geometrical top bases 16, 26 (referred herein to as upper rods), opposite to the lower rod 1, are made parallel with the lower rod 1, so that the upper rod 16 in the first, 4-joint linkage is constantly kept parallel with the upper rod 26 in the second, 4-joint linkage.

The upper rods 16, 26 have a respective extended arm fixed on them. In the case of FIG. 1, the upper rod 16 in the first, 4-joint linkage 14 has the first extended arm 12 fixed in a substantially perpendicular direction. Likewise, the upper rod 26 in the second, 4-joint linkage 24 has the second extended arm 22 fixed in a substantially perpendicular direction. Since the upper rod 16 in the first, 4-joint linkage is kept in parallel with the upper rod 26 in the second 4-joint linkage, the first and second extended arms 12, 22, which are perpendicular to the two upper rods, are also kept parallel with each other. In this manner, the seizing area X, formed between the first and second extended arms 12, 22, can be kept at a substantially equal distance. The terms "parallel" and "equal distance" in a strictly geometrical sense may not be applied to the present disclosure, because a more or less error in dimension may occur in an actual fabrication. However, it should be understood that these terms are encompassed in this invention insofar as the function disclosed herein can be performed.

In the case of FIG. 1, the first and second extended arms 12, 22 are respectively fixed perpendicularly to the upper rod 16 in the first, 4-joint linkage 14 and to the upper rod 26 in the second, 4-joint linkage 24. These extended arms, however, may respectively be fixed at an angle. For example, the first extended arm may be fixed at an angle of 45° to the right direction on the upper rod of the first, 4-joint linkage, and the second extended arm may also be fixed at an angle of 45° to the right direction on the upper rod of the second, 4-joint linkage. Thus, the first and second extended arms are still kept in a parallel position to obtain a parallel relationship in the seizing area. Aside from the fixation of the extended arms at an angle with respect to the upper rods, the extended arms may be fixed substantially perpendicularly to the rods and yet the extended arms themselves may be bent or curved in an intermediate portion to achieve a similar effect.

In the case of FIG. 1, a portion of the first shank 11 constituting the first tong member 10 is utilized as one rod which constitutes the first, 4-joint linkage. That is, an upper rod pivot A is provided in the vicinity of the front end of the rod-shaped shank 11, and a lower rod pivot B is provided in the intermediate portion, so that the upper rod 16 and the lower rod 1, both being of the same length, are respectively connected pivotably to the above pivots. By this configuration, the stretch AB between the upper rod pivot A and the lower rod pivot B serves to constitute a left rod 15 in the first, 4-joint linkage 14. Also, the upper rod 16 and the lower rod 1 are respectively connected, pivotably via the upper right pivot D and the lower right pivot C, to the right rod link 17 which is substantially of the same length as the left rod 15, so that the first, 4-joint linkage is constituted by the upper rod 16, the right rod link 17, the lower rod 1, and the left rod 15 which is a portion of the first shank 11. In this manner, when a portion of the first shank 11 in the first tong member 10 is made common with the left rod 15 in the first, 4-joint linkage, a cost of manufacture can be reduced by employing a small number of components and simplifying the structure. Similarly, in the second tong member 20 as well, the second shank 21 can be in common with the right rod 25 in the second, 4-joint linkage 24. To explain as seen in FIG. 1, the second, 4-joint linkage 24 is made up of the upper rod 26 and the lower rod 1 which are connected pivotably to and extended leftward from the upper rod pivot E and the lower rod pivot C, so that the left rod link 27 is connected to the upper left pivot F and the lower left pivot B which are the pivots situated at the front ends of the rods 26, 1, resulting in the formation of the second, 4-joint linkage 24. Also in the case of FIG. 1, the pivots can be made common by coinciding the lower rod pivot B with the lower left pivot B for a reduced number of components and for a simplified process of fabrication. Likewise, the lower right pivot C is made common with the lower rod pivot C.

Figure 3:
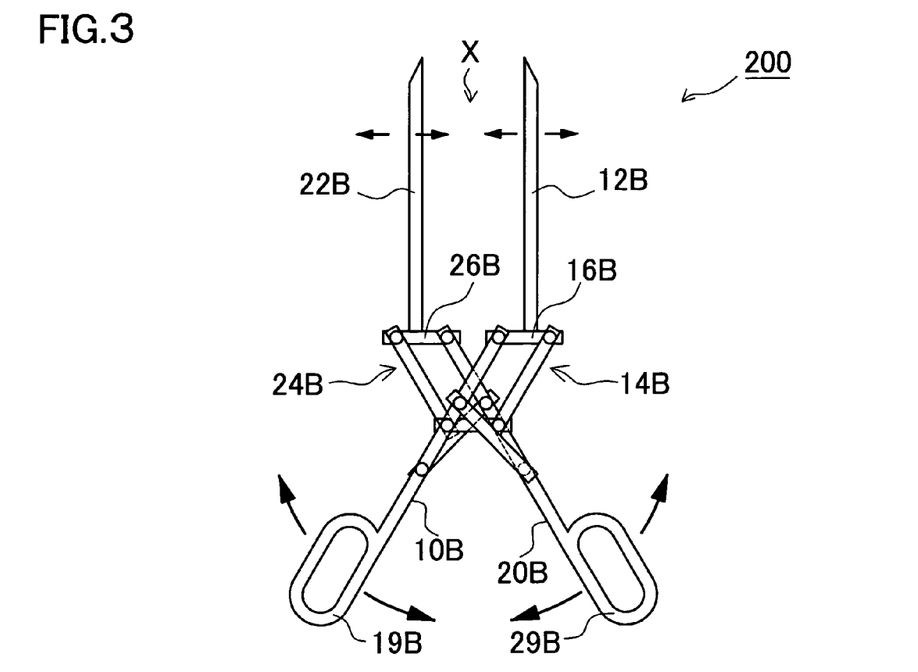
FIG. 3 is a schematic view of the tongs according to a second embodiment of the invention, in which the seizing area is in an open position.
Figure 4:
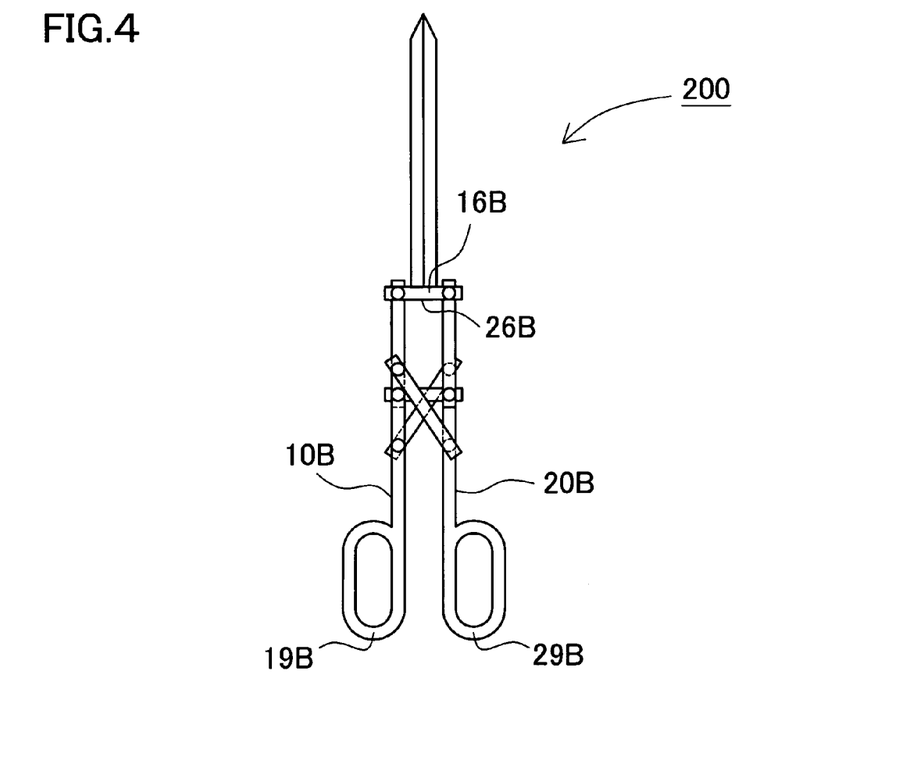
FIG. 4 is a schematic view of the tongs shown in FIG. 3, in which the seizing area is in a closed position.

In the case of FIG. 1, the left and right rod links in the second, 4-joint linkage 24 is extended slightly longer than the left and right rod links in the first, 4-joint linkage. By this configuration, when the seizing area X is move to its closed position by closing the actuating tails 19, 29 of the first and second tong members 10, 20, as shown in FIG. 2, the upper rod 16 in the first, 4-joint linkage will not overlap with the upper rod 26 in the second, 4-joint linkage, so that a contact due to the thickness in the two upper rods need not be taken into consideration. However, like in the tongs 200 shown in FIGS. 3 and 4 as the second embodiment of this invention, the first, 4-joint linkage 14B and the second, 4-joint linkage 24B may be made substantially the same in shape and dimension. In this case, as shown in FIG. 4, when the seizing area X is moved to its closed position by closing the actuating tails 19B, 29B of the first and second tong members 10B, 20B, the upper rod 16B in the first, 4-joint linkage overlaps with the upper rod 26B in the second, 4-joint linkage. To prevent such a mutual contact from hampering the pivotal movement, it is required to work out a proper thickness and/or to design a stepped structure. Nevertheless, the same structure employed in the first and second tong members 10B, 20B constituting the left and right halves of the tongs will advantageously enable a fabrication process to be simplified for a lower cost of manufacture.

Auxiliary Link

In this manner, it becomes possible to keep the seizing area in a parallel position by combining the two 4-joint linkages and having one rod in common. With the tongs 100, the distance between the first and second extended arms 12, 22 can be adjusted by operating the apertures 13, 23 formed at the actuating tails 19, 29 of the first and second tong members 10, 20 to pivot and incline the left and right rods in the 4-joint linkages 14, 24. On the other hand, when an operator holds the actuating tails of the first and second tong members to apply a stress for opening and closing of the tails, the stress may sometimes be dispersed at the various bending points included in the 4-joint linkages, making it difficult to properly adjust a desired opening width in the seizing area. In such an instance, it is desirable that the lower rod, i.e., the common rod, be stabilized so that the operation or motion of the actuating tails will be smoothly transferred for the opening and closing of the seizing area. For this purpose, it is preferred that the first and second tong members be connected via an auxiliary link. In the case of FIG. 1, the first auxiliary link 18 has a pivot respectively at opposite ends, in which one end of the link is connected to the first tong member 10 and the other end is connected to the second tong member 20. For purposes of such an arrangement, the first tong member 10 has a hole G opened intermediate the lower rod pivot B and the actuating tail 19, for connecting the first auxiliary link to the first tong member, while the second tong member 20 has a hole H opened intermediate the lower rod pivot C and the upper rod pivot E, for connecting the first auxiliary link to the second tong member. By this configuration, when a stress is applied to operate the actuating tails 19, 29 of the first and second tong members 10, 20, such a stress as to needlessly bend the bending portions in the 4-joint linkages 14, 24 is less likely to be dispersed, resulting in an easy and smooth adjustment of the opening width in the seizing area X.

Further, when a plurality of auxiliary links are prepared in the tongs, a more stable operation will be realized by arranging those auxiliary links to intersect each other. In the case of FIG. 1, along with the first auxiliary link 18, there is a second auxiliary link 28 connected between the second tong member 20 and the first tong member 10. To allow the second auxiliary link to be connected, the first tong member 10 has a hole I opened between the lower rod pivot B and the upper rod pivot A, for connecting the second auxiliary link to the first tong member, while the second long member 20 has a role J opened between the lower rod pivot C and the actuating tail 29, for connecting the second auxiliary link to the second tong member. By connecting these connection holes to the second auxiliary link 28 in a pivotable manner, the first and second auxiliary links 18, 28 can intersect each other for interconnecting the first tong member 10 with the second tong member 20. Thus, the operation or motion of the actuating tails 19, 29 can be even more smoothly transferred for the opening and closing of the seizing area X, owing to the proper guide by these auxiliary links.

Linkage

To describe further, the above-mentioned linkage is so designed to operate organically and smoothly by a conjoint movement of five total sets of 4-joint linkages which consist of two sets of 4-joint, parallel linkages and three sets of 4-joint, intersectional linkages. However, as seen in FIG. 1, the lower rod pivot (lower left pivot) B can be located at any optional point between the hole I for connecting the second auxiliary link to the first tong member and the hole G for connecting the first auxiliary link to the first tong member, with the exception of the exact locations of the hole I (for connecting the second auxiliary link to the first tong member) and the hole G (for connecting the first auxiliary link to the first tong member).

Figure 5:
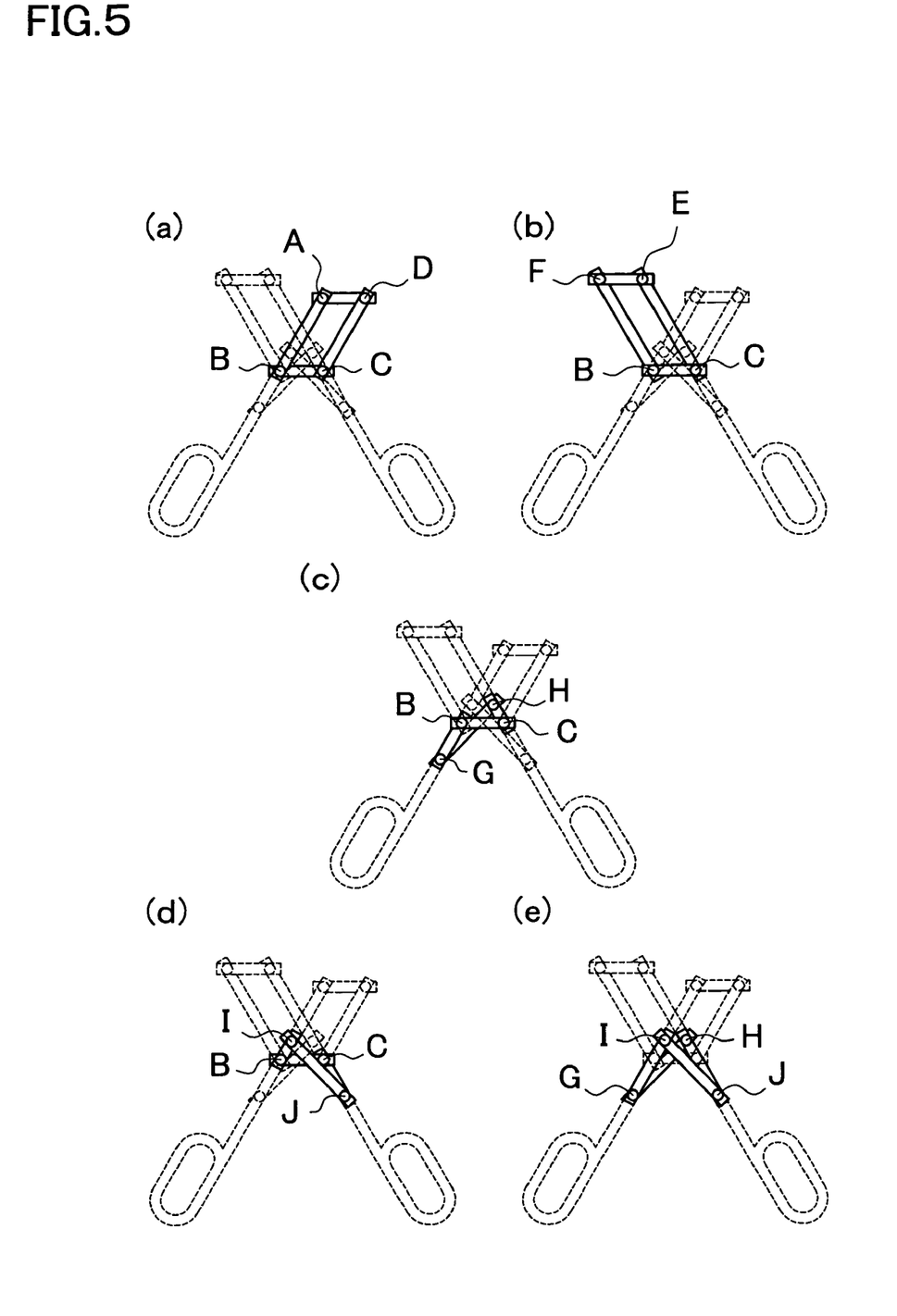
FIG. 5 is a view illustrative of a 4-joint parallel linkage and a 4-joint intersectional linkage.

To describe further, the two sets of 4-joint, parallel linkages refer to the 4-joint, parallel linkage consisting of the parallelogram ABCD as shown in FIG. 5(a) and the 4-joint, parallel linkage consisting of the parallelogram BCEF as shown in FIG. 5(b). The three sets of 4-joint, intersectional linkages, on the other hand, refer to the 4-joint, intersectional linkage consisting of BCHG as shown in FIG. 5(c), the 4-joint, intersectional linkage consisting of BCJI as shown in FIG. 5(d), and the 4-joint, intersectional linkage consisting of GHJI as shown in FIG. 5(e). As mentioned below, these linkages can perform their basic function, without the rod BC in FIGS. 5(a) and 5(b), without the rod GH in FIG. 5(c), and without the rod JI in FIG. 5(d). In such a case, the 4-joint, intersectional linkage is reduced from three sets to a single set. While the reduced number of components in a set disposing of a particular rod may thus yield a simplified structure, it is the most preferable that all the above-enumerated linkages be provided to obtain a smoother motion.

Referring to FIG. 2, various center distances are defined as follows: "Ic-Bc" for the distance between the central point IC in the hole I for connecting the second auxiliary link to the first tong member and the central point in the lower rod pivot (lower left pivot) B, "Bc-Cc" for the distance between the central point Bc and the central point Cc of the lower rod pivot (lower right pivot) C; "Cc-Jc" for the distance between the central point Cc and the central point Jc in the hole J for connecting the second auxiliary link to the second tong member; and "Jc-Ic" for the distance between the central point Jc and the central point Ic. Thus, when the ratio of "IC-Bc" to "Bc-Cc", "Cc-Jc" and "Jc-Ic" is set to be approximately 1:3:3:5 by length of distance, the seizing area X shown in FIG. 1 can reach its maximum width. Likewise, because the tongs shown in FIGS. 1 and 2 have the linkage configured substantially symmetrically, side for side, the center distances are defined as follows: "Hc-Cc" for the distance between the central point Hc in the hole H for connecting the first auxiliary link to the second tong member and the central point Cc, "Cc-Bc" for the distance between the central point Cc and the central point Bc; "Bc-Gc" for the distance between the central point Bc and the central point Gc in the hole G for connecting the first auxiliary link to the first tong member; and "Gc-Hc" for the distance between the central point Gc and the central point Hc. In this case as well, the ratio of (Hc-Cc):(Cc:Bc):(Bc-Gc):(Gc-Hc) is also set to be approximately 1:3:3:5 by length of distance.

Actuating Tail

As mentioned above, the actuating tails 19, 29 of the first and second shanks 11, 21 have apertures 13, 23 defined respectively for engaging the operator's thumb or finger. By this arrangement, the first and second tong members 10, 20 which are intersectionally interconnected can be easily manipulated by the opening and closing operation using the thumb and finger. For example, when the thumb is engaged in the second aperture 23 in the second shank 21, and the first finger is engaged in the first aperture 13 in the first shank 11, the actuating tails 19, 29 can travel in an arcuate manner like when opening and closing a pair of scissors. The opening width in the seizing area can correspondingly be adjusted, with the two extended arms being kept in a parallel relationship.

It will be apparent that the seizing area X can constantly be kept in a parallel position owing to the above-mentioned configuration. In the case of conventional tongs which are intersected into an X-formation, with a load point, a fulcrum and an effect point existing, when the load point is pivoted on the fulcrum, the effect point travels through an arc. With such a conventional structure, the effect point, comparable to the seizing area X, begins to seize an article in an oblique angularity instead of a parallel state. Resultantly, for example, if a circular article is seized with planar extended arms, the article is prone to slip off and drop out of the extended arms, and if an excessive stress is applied in an attempt to hold the article firmly, the portion of contact is subjected to a locally increased stress, leading to the article being deformed or damaged. Constrastingly, in the case of the tongs according to the inventive embodiment, a stress can be applied to the article equally from the left and right sides in a parallel position, in which a local stress is unlikely to be concentrated, and so even a circular article can be advantageously seized and held with a weaker stress. Further, unlike scissors and other instruments having a single fulcrum in an X-formed intersection, the present embodiment is of such a structure as not to open and close obliquely, so that an extend occupied by the seizing area can be reduced to minimum. It is, therefore, advantageous that the extended arms 12, 22 in a parallel relationship can be easily engaged into a deep container. For example, the inventive tongs can be utilized as a pair of tweezers to be used for fabricating a miniature ship contained in a transparent bottle.

The tongs in this configuration can also be suitably utilized for evenly sandwiching an article, being used, for example, as kitchen tongs and general-purpose working tongs. The inventive tongs are also suitable as a medical instrument like forceps. In addition to a manual operation, the actuating tails in the tongs can be automatically manipulated when connected to machinery. When connected to machinery, the actuating tails need not be equipped with thumb or finger engaging apertures, but the tails can be connected either directly to a driving source or via a power transfer mechanism such as an interlink. Machine-driven tongs can be conveniently applied for work in which an object with a larger size of diameter is to be seized. One of the possible applications is a gripping manipulator as used for gripping and inverting containers such as glass bottles and plastic (e.g., PET) bottles which are automatically cleaned in a washing machine. The tongs are used for seizing the neck portion of such bottles, sideways from opposite sides. Furthermore, when equipped with a pantographic arm mechanism hung on an elevated crane for example, the tongs can be suitably employed in a wide range of industrial fields aiming an factory automation, like in a steel making factory where slabs are transferred from place to place or otherwise handled.

While the first and second shanks 11, 21 shown throughout the drawings including FIG. 1 are illustrated in a straight shape for the purposes of simplicity and clarity, the shanks can naturally be somewhat curved or bent in their entirety or in part. Likewise, the rods and rod link constituting the 4-joint linkage can also be curved or bent in their entirety or in part insofar as their function of maintaining a parallel relationship is not spoiled.

Extended Arm

Figure 6:
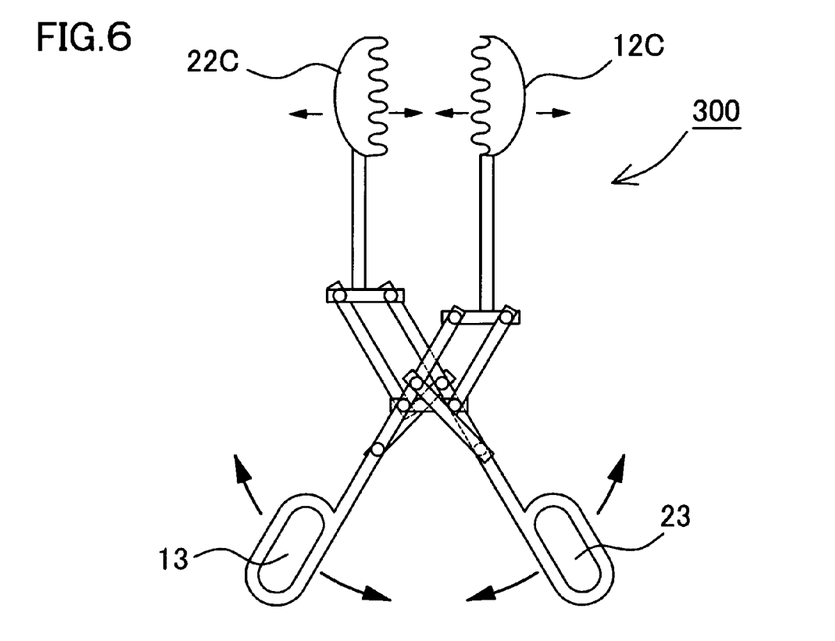
FIG. 6 is a schematic view of the tongs according to a third embodiment of the invention, in which the seizing area is in an open position.

Depending on applications, various modifications or alterations can be made to the shape of the extended arms. In the case of FIG. 1 as described and illustrated above, the first extended arm 12 and the second extended arm 22 have (oppositely) facing planar surfaces, while exemplarily in the case of the tongs shown in FIG. 6 as a third embodiment of the invention, there are buckets or ladle bowls mounted to the front ends of the extended arms 12C, 22C, so that an article to be seized may be enclosed in the buckets or ladle bowls for a better seizing ability. Additionally, the peripheral lips of the buckets or ladle bowls, i.e., the peripheral portions where the first and second extended arms 12C, 22C meet each other, may be formed with a waved shape, such that the two lips may complimentarily engage each other for the closest possible closure of the buckets or ladle bowls. The article to be seized can thus be contained in the buckets or bowls in a more secure manner.

Cut Surface

Figure 7:
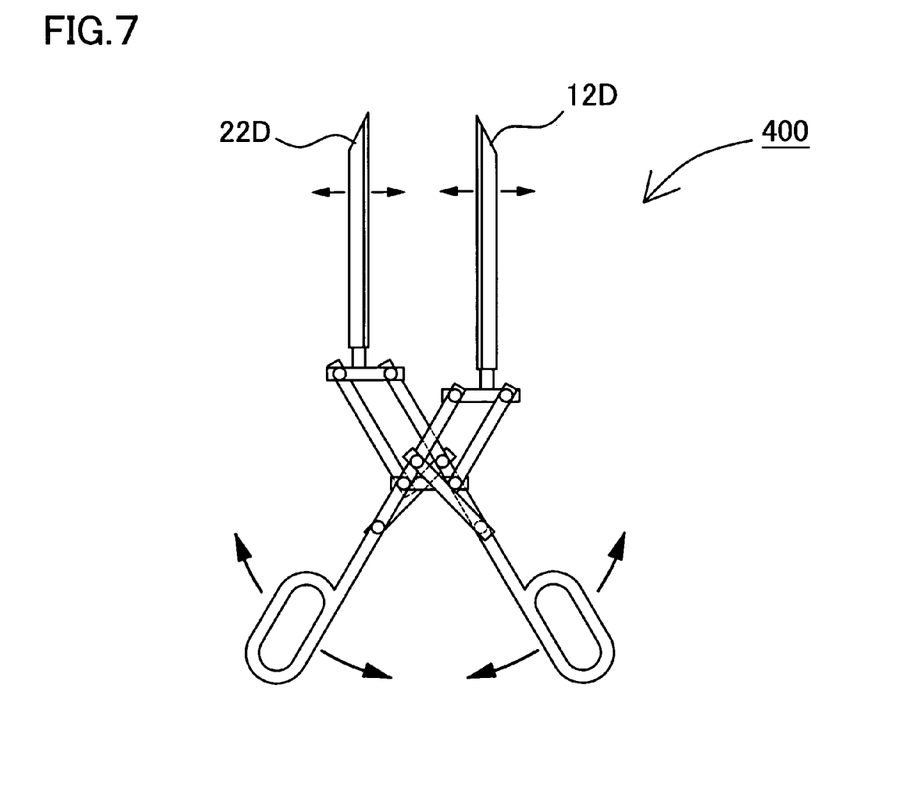
FIG. 7 is a schematic view of the tongs according to a fourth embodiment of the invention, in which the seizing area is in an open position.

The tongs can also have a pair of cutting blades formed on the extended arms. For example, in the case of the tongs 400 shown in FIG. 7 as a fourth embodiment of the present invention, there are sharp cutting blades mounted to the facing portions of the first and second extended arms 12D, 22D. By this arrangement, the two blades can be utilized as a pair of scissors for cutting an article. This particular pair of scissors, different from conventional scissors which are intersected into an X-formation, can have an advantage that an article is cut into a clear cut edge, with the two blades being tangentially oriented and kept in a parallel relationship. That is, in the case of conventional scissors in an X-formation, the blades contact and enter an article, at an non-tangential angle, to form a cut surface. Particularly when an article is in a circular or cylindrical shape, the cutting area of the article will be subjected to an impartial stress, which is likely to cause a warp or deformation to the circularity. Constrastingly, with a method of cutting an article entering the blades from sideways in a parallel relationship as embodied in the present disclosure, an evenly applied force is not likely to cause a deformation to the article, assuring a high advantage that a circular article is cut with its original form being maintained.

With regard to a configuration of the cutting blades, when the seizing area is in its closed position, the edge of the cutting blade on the first extended arm is adapted to meet with its counterpart on the second extended arm, in such a manner that the two blades terminates in an edge-to-edge abutment with each other over their entire edge line, without advancing further inwardly. In another configuration, the two blades may be arranged to advance further inwardly to pass each other, like a pair of scissors coming into their closed, overlapped position, The blades need not be formed over the entire length of the extended arms. It is sufficient to form the blades over a part of the length. By this arrangement, the article can be either seized or cut interchangeably, depending on the type of work to be carried out. Needless to say, the above-mentioned planar surface, bucket or blade may be optionally combined with each other on each of the extended arms. By mounting such cutting blades on the extended arms, the tongs can be utilized as handicraft or kitchen scissors as well. It should be noted that an instrument serving to perform a scissor-like function in part or over the entirety of the extended arms is encompassed in the inventive tongs, regardless of its proper naming.

Figure 8:
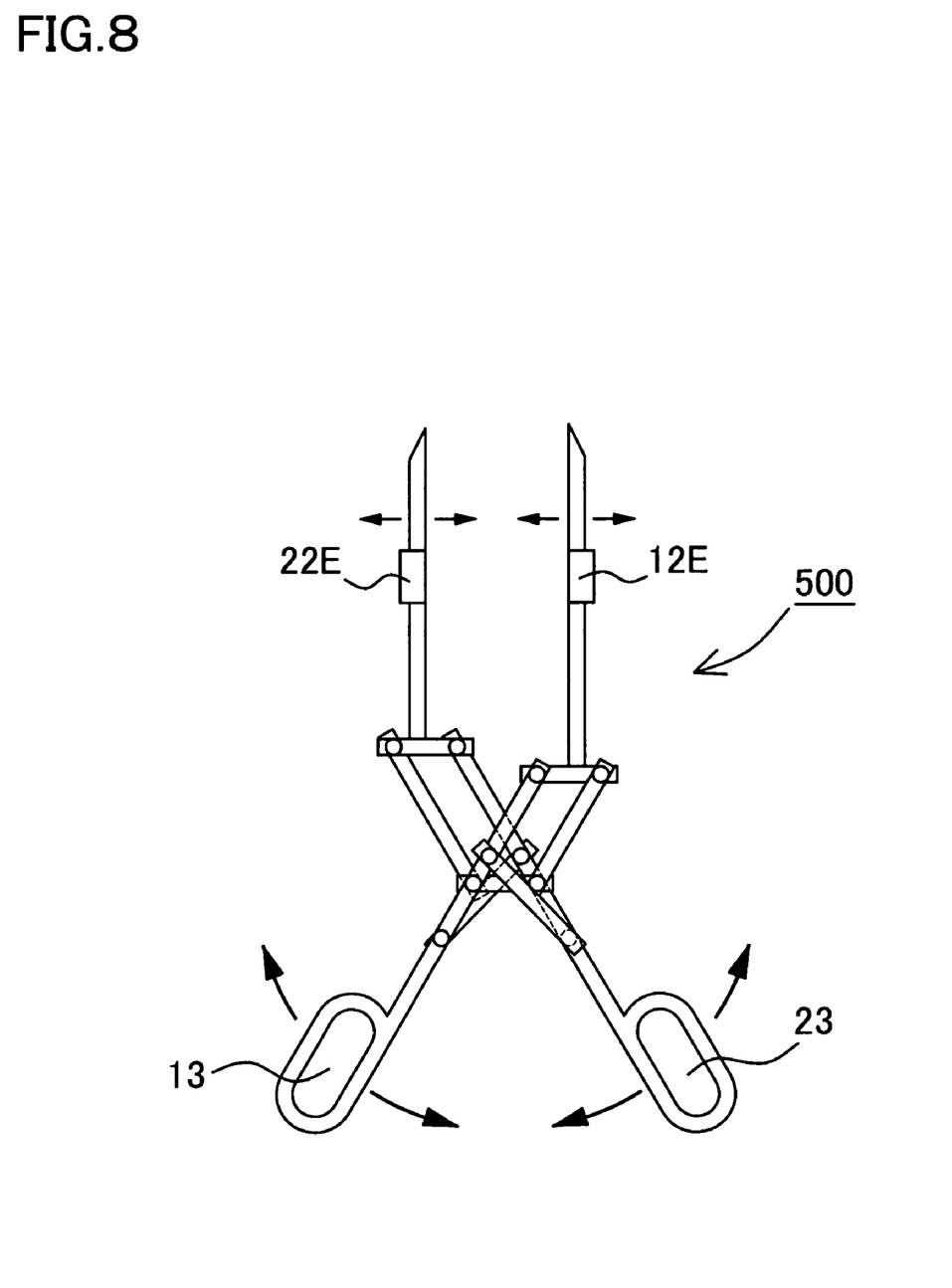
FIG. 8 is a schematic view of the tongs according to a fifth embodiment of the invention, in which the seizing area is in an open position.

Optionally, a heating element can be attached to the extended arm. For example, in the case of the tongs 500 shown in FIG. 8 as a fifth embodiment of the present invention, there is a heating element mounted to one or both of the facing portions in the first and second extended arms 12E, 22E. By this arrangement, the extended arm will function to heat, and thus be suitably used for materials to be thermally processed. Further, when designed to control the temperature of the heating element, the tongs can be utilized as a processing convenience tool for working over a wide range of temperatures, for example, as a hot iron, a soldering iron, a cloth creaser, and a simple tool for cutting or folding thermoplastic materials. By this configuration, it is also possible to move, open or close, in a parallel position without an angle, the extended arms 12E, 22E which have a temperature-controllable heating source. This is especially useful when a constricted working area or other areas should not be contacted by the extended arm, i.e., the heating element.

Figure 9:
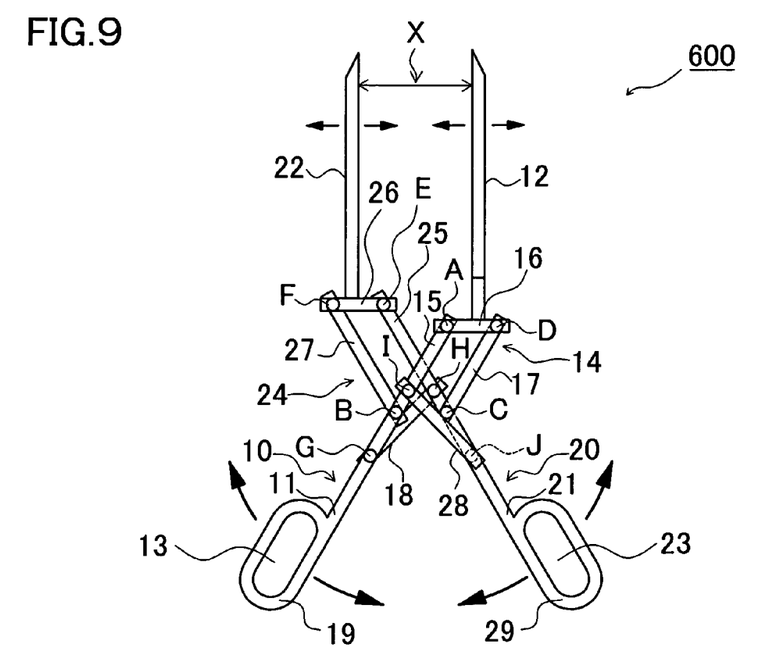
FIG. 9 is a schematic view of the tongs according to a sixth embodiment of the invention, in which the seizing area is in an open position.
Figure 10:
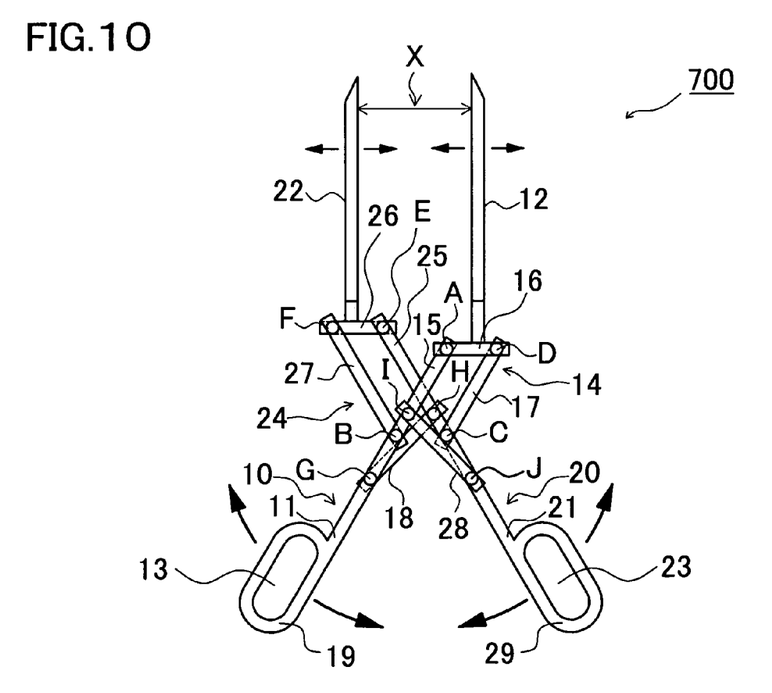
FIG. 10 is a schematic view of the tongs according to a seventh embodiment of the invention, in which the seizing area is in an open position.

The tongs can also be prepared without the common rod (the lower rod). In the case of the tongs 600 shown in FIG. 9 as the sixth embodiment of the present invention and also in the case of the tongs 700 shown in FIG 10 as the seventh embodiment, the two tongs are configured without the lower rod 1 included in the tongs 100 shown in FIG. 1. When so configured, some ricketiness may occur in motion of the tongs due to some dimensional error in the design or fabrication, however such a variation has an advantage in that a smaller number of components employed will contribute to a reduced cost of manufacture owing to a smaller number of manufacturing processes. It should be noted that the sequential process of joining individual members, such as the link and the shank, can be optionally designed. To prevent individual members from contacting each other and hampering a smooth pivotal motion in operation, the thickness of the link or the shank can also be suitably modified or the members may be partially cut out to have an interfacial step against each other. By way of example, when a person views the tongs 600 as shown in FIG. 9, the upper rod 26 has the pivot connected by using a fastener such as a bolt and a pin, such that the upper rod 26 appears nearer to the person in its combination with the right rod 25 and the left rod link 27. In addition, there is an interfacial step formed in the joint, so that the first extended arm 12 may be placed behind as viewed by the person. In the case of the tongs 700 shown in FIG. 10, on the other hand, while being configured in substantially the same manner as the tongs 600 shown in FIG. 9, the upper rod 26 is placed behind as viewed by the person in its combination with the right rod 25 and the left rod link 27. In addition, there is an interfacial step formed so that the first and second extended arms 12, 22 may be placed behind as viewed by the person. In this manner, by suitably changing the overlapping side or face and the thickness of individual members, the tongs are configured so as not to hamper a pivotal motion.

The tongs in accordance with the present invention can be suitably utilized as tongs for seizing food products such as spaghetti and vegetables, also serving well as handicraft pincers, medical forceps, and a scissor-equipped holding device.

As this invention may be embodied in several forms without departing from the spirit or essential characteristics thereof, the present embodiment is therefore illustrative and not restrictive, since the scope of the invention is defined by the appended claims rather than by the description preceding them, and all changes that fall within the metes and bounds of the claims or equivalence of such metes and bounds thereof are therefore intended to be embraced by the claims. This application is based on applications No. 2005-194,429 filed in Japan on Jul. 1, 2005, the content of which is incorporated hereinto by reference.

What is claimed is:

1. A pair of tongs in a scissor-like configuration, the tongs comprising:

a first tong member including a first shank elongated in one direction, a first actuating tail at one end of the first shank, and a first arm for seizing and lifting an article, the first arm being extended from an opposite end of the first shank relative to the first actuating tail; and a second tong member including a second shank elongated in one direction, a second actuating tail at one end of the second shank, and a second arm for seizing and lifting the article, the second arm being extended from an opposite end of the second shank relative to the second actuating tail;

wherein the first and second tong members are pivotably interconnected on one or more fulcrums, so that a distance in an article-seizing area defined between the first and second arms is capable of being adjusted by operating the respective actuating tails of the first and second tong members, the first tong member being provided with a first, parallelogrammatic, 4-joint linkage comprising two pairs of opposite rods, in which both pairs of opposite rods are configured to be substantially equal, in length, to each other, the second tong being provided with a second, parallelogrammatic, 4-joint linkage comprising two pairs of opposite rods, in which both pairs of opposite rods are configured to be substantially equal, in length, to each other, the first and second 4-joint linkages having one of the foregoing rods in common, the first 4-joint linkage having the first arm mounted to the rod that is opposite to the common rod, the second 4-joint linkage likewise having the second arm mounted to the rod that is opposite to the common rod, wherein, when the first and second actuating tails in the first and second tong members are operated in an arcuate manner, an opening width in the article-seizing area is configured to be capable of being adjusted, while the first and second arms are maintained in a substantially parallel relationship with each other, the first tong member further including a first auxiliary link provided with a pivot respectively at opposite ends thereof, the first auxiliary link being connected with the first tong member at one of the pivots and with the second tong member at the other of the pivots.

2. The tongs as recited in claim 1, wherein the second tong member further comprises a second auxiliary link provided with a pivot respectively at opposite ends thereof, the second auxiliary link being connected to the second tong member at one of the pivots and to the first tong member at the other of the pivots.

3. The tongs as recited in claim 2, wherein a portion of the first shank is configured to be common with one rod constituting the first, 4-joint linkage.

4. The tongs as recited in claim 1, wherein the rods adjacent to the common rod in the second, 4-joint linkage are configured to be longer than in the first, 4-joint linkage.

5. The tongs as recited in claim 1, wherein the second, 4-joint linkage is configured to be in substantially the same shape and dimension as the first, 4-joint linkage.

6. The tongs as recited in claim 1, wherein each of the first and second actuating tails has an aperture for accommodating an operator's thumb or finger.

7. The tongs as recited in claim 1, wherein each of the first and second arms are respectively provided with a cutting knife.

8. The tongs as recited in claim 1, wherein at least one of the first and second arms is provided with a heating element.

9. A pair of tongs in a scissor-like configuration, the tongs comprising:

a first tong member including a first shank elongated in one direction, a first actuating tail at one end of the first shank, and a first arm for seizing and lifting an article, the first arm being extended from an opposite end of the first shank relative to the first actuating tail; and a second tong member including a second shank elongated in one direction, a second actuating tail at one end of the second shank, and a second arm for seizing and lifting the article, the second arm being extended from an opposite end of the second shank, relative to the second actuating tail;

wherein the first and second tong members are pivotably interconnected on one or more fulcrums, so that a distance in an article-seizing area defined between the first and second arms is capable of being adjusted by operating the first and second actuating tails of the first and second tong members, the first tong member further including a first, 4-joint linkage comprising two pairs of opposite rods in which an opposed pair of substantially parallel rods are substantially equal, in length, to each other, the second tong member further including a second, 4-joint linkage comprising two pairs of opposite rods in which an opposed pair of substantially parallel rods are substantially equal, in length, to each other, the first, 4-joint linkage having the first arm mounted to a rod which is pivotably extended across one of the opposed pairs of substantially parallel rods of the first 4-joint linkage, the second, 4-joint linkage likewise having the second arm mounted to a rod which is pivotably extended across one of the opposed pairs of substantially parallel rods of the second 4-joint linkage, the first tong member further including a first auxiliary link provided with a pivot respectively at opposite ends thereof, the first auxiliary link being connected with the first tong member at one of the pivots and with the second tong member at the other of the pivots, the second tong member further including a second auxiliary link provided with a pivot respectively at opposite ends thereof, the second auxiliary link being connected with the second tong member at one of the pivots and with the first tong member at the other of the pivots, wherein, when the first and second actuating tails in the first and second tong members are operated in an arcuate manner, an opening width in the article-seizing area is configured to be capable of being adjusted, while the first and second arms are maintained in a substantially parallel relationship with each other.

* * * * *